(12) United States Patent
Hendrix

(10) Patent No.: US 6,500,450 B1
(45) Date of Patent: *Dec. 31, 2002

(54) COMPOSITION FOR TREATING MIGRAINE HEADACHES

(76) Inventor: Curt Hendrix, 17401 Ventura Blvd., Encino, CA (US) 92705

(*) Notice: Subject to any disclaimer, the term of this patent is extended or adjusted under 35 U.S.C. 154(b) by 0 days.

This patent is subject to a terminal disclaimer.

(21) Appl. No.: 09/560,306

(22) Filed: Apr. 27, 2000

Related U.S. Application Data

(63) Continuation-in-part of application No. 09/104,862, filed on Jun. 25, 1998, now Pat. No. 6,068,999.

(51) Int. Cl.⁷ .......................... A61K 47/00; A61K 33/06
(52) U.S. Cl. ........................................ 424/439; 424/682
(58) Field of Search .................... 435/195.1; 424/195.1, 424/439, 465

(56) References Cited

U.S. PATENT DOCUMENTS

| | | | |
|---|---|---|---|
| 4,704,279 A | 11/1987 | Hancock | 424/195.1 |
| 4,758,433 A | 7/1988 | Johnson et al. | 424/195.1 |
| 5,273,759 A | 12/1993 | Simmons | 424/195.1 |
| 5,466,451 A | 11/1995 | Beuscher et al. | 424/195.1 |
| 5,538,959 A | 7/1996 | Mauskop | 514/165 |
| 6,068,999 A | * 5/2000 | Hendrix | 435/195.1 |

FOREIGN PATENT DOCUMENTS

| | | |
|---|---|---|
| WO | WO 9622774 | 8/1996 |
| WO | WO 99/22774 | 8/1996 |

OTHER PUBLICATIONS

Donald Brown, N.D., Alan Gaby, M.D. Ronald Reichert, N.D. Clinical Applications of Natural Medicine, *Migraine*, Feb. 1996, p. 3–14.

J. Durlach, *Present, and Future of Magnesium Research*, Journal of Japanese Society for Magnesium Research 1993, 12, 2:113–135, Apr. 13, 2000, page 1 of 21.

Health Care Professionals Product Detail Sheet, MIGRA–LIEVE, Adietary Supplement Supporting Cerebrovascular Tone, Dec. 1, 1997.

* cited by examiner

*Primary Examiner*—Thurman K. Page
*Assistant Examiner*—Blessing Fubara
(74) *Attorney, Agent, or Firm*—Koppel, Jacobs, Patrick & Heybl; Michael J. Ram

(57) ABSTRACT

The present invention relates to a dietary supplement for the treatment of migraine headache. An extract of the feverfew plant containing parthenolide in combination with magnesium, with or without riboflavin, provided significant reduction of migraine headaches and the associated symptoms. The magnesium is present as a combination of magnesium oxide and a magnesium salt of an organic acid. The ratio of magnesium to parthenolide was about 450:1

23 Claims, 1 Drawing Sheet

COMPOSITION FOR TREATING MIGRAINE HEADACHES

This application is a Continuation-in-Part of U.S. patent application Ser. No. 09/104,862 filed Jun. 25, 1998 now U.S. Pat. No. 6,068,999 issued Apr. 27, 2000.

FIELD OF THE INVENTION

The present invention provides a dietary supplement which supplies a combination of prophylactic and restorative components which assist the body in maintaining normal cerebrovascular tone and reduces the symptoms of migraine headaches.

BACKGROUND OF THE INVENTION

Migraine has been a well-known medical problem for over 5,000 years and represents one of the most investigated types of head pain. Epidemiological research has shown that in the United States, 18% of women and 6% of men suffer from migraine headaches. This extrapolates to approximately 18 million females and 5.6 million males over the age of 12 with this disorder. The prevalence of migraine, according to the Center for Disease Control, has increased 60% from 1981 to 1989. While migraine can occur at any age, 30% of migraine sufferers report their first attack before the age of ten, and the condition is most common in adolescents and young adults. The economic impact of migraine is staggering, with annual cost of the disease estimated at 18 billion dollars.

The basic cause of migraine is still unknown. Although genetics may play a role, with 50 to 70% of migraine sufferers reporting a familial occurrence, no consistent biochemical or physiological characteristic has yet to be identified in the relatives of those afflicted with the conditions.

There are several pathophysiological views on the origin of migraine. While not mutually exclusive, these views include the a) Êvascular theory, b) central theory, c) neurogenic Inflammation theory and d) platelet theory.

a. Vascular Theory

In 1938, Graham and Wolff, two of the period's most preeminent headache researchers, developed the vascular hypothesis of migraine. They suggested that contraction of the intracranial arteries caused a reduction in blood flow to the visual cortex in the occipital lobe, resulting in the focal neurological symptoms ("aura") that accompany a migraine episode. As a consequence, the head pain that followed was the result of extra-cranial vasodilatation of the external carotid system, along the nerve compression in the carotid artery wall. These conclusions were based on the observation that the vasoconstricting drug ergotamine tartrate dampened pulsation of the superficial temporal artery (an end branch of the external carotid artery), resulting in migraine pain relief.

Despite the fact that the vascular model has been a dominant concept in migraine pathophysiology, several difficulties arising from this theory have been noted. These include the fact that during a common migraine attack, only minor changes in cerebral blood flow have been noted. Furthermore, oligemia, a phase of reduced blood flow, lasts for several hours longer than the aura. Lastly, the reduced blood flow is not sufficient to induce ischemia, alter neuronal function, and produce the aura phase. As a consequence of these criticisms, the central theory of migraine has been proposed.

b. Central Theory

The central theory suggests that spreading oligemia is the consequence of spreading neuronal depression, which begins as a result of decreased neuronal function in the occipital poles of the brain and progresses forward at a rate of two to three millimeters per minute. The spreading depression involves the depolarization of neurons and has associated with it marked cellular ionic abnormalities. The resulting lowered levels of cellular magnesium increase the likelihood of this type of spreading neuronal depression occurring. This repression of neural function results in a spreading oligemia that can last up to four to six hours. It progresses anteriorly, in a wave-like fashion, over the areas perfused by the middle and posterior cerebral arteries, temporarily impairing cortical vascular functioning. As result, the aura of migraine may be the result of spreading depression, "a phenomenon originating within brain neurons and involving cerebral blood vessels only secondarily."

c. Neurogenic Inflammation Theory

While the concept of spreading neuronal depression and oligemia may explain the migraine aura, it does not account for ensuing headache. Migraine head pain may be the result of inflammation in the trigeminovascular system (TVS). This theory suggests that the trigeminal nerve fibers innervating cranial vessels are an important component of an elaborate defense network protecting the brain from an actual or perceived insult. Inflammatory neurotransmitters such as substance P, calcitonin gene-related peptide and neurokinin A are released by the fifth cranial nerve. This release signals adjacent meningeal blood vessels to dilate. The resulting neurogenic inflammation sensitizes the neurons and this induces head pain. It is interesting to note that stimulation of the presynaptic serotonin receptor (5HT-1), blocks the release of substance P, thus preventing inflammation and pain.

d. Platelet Theory

Many researchers have felt that serotonin (5HT) is the specific neurochemical cause of migraine. Platelets contain all of the 5HT normally present in blood, and after they aggregate, 5HT is released, resulting in a potent vasoconstricting effect. During migraine attack, platelet 5HT increases in the aura phase and diminishes in the headache phase. Following a migraine attack, there is an increase in urinary 5-hydroxyindolacetic acid (5-HIAA), the main metabolite of serotonin. It is interesting to note that "serotonergic circuits are believed to be involved in modulation of sleep cycles, pain perception, and mood, all important factors in the pathogenesis of migraine." For example, "a decrease in the firing rate of serotonergic neurons of the midbrain dorsal raphe nucleus occurs with sleep, correlating with the observation that sleep often aborts a migraine attack."

However, serotonin may not be the only vasoactive chemical involved in the pathogenesis of migraine. Histamine, tyramine, catecholamines (norepinephrine and dopamine), prostaglandin E and free fatty acids may all have important roles to play in migraine pathogenesis.

Existing Treatments—Abortive Therapy

For the migraine sufferer, there are a wide variety of therapeutic approaches both pharmacologic and non-pharmacologic. However, for practical reasons the management of migraine can be divided into a) abortive treatment and b) preventative treatment.

a. Abortive Treatment

An abortive treatment of migraine simply addresses the symptoms. Only pharmacological interventions with analgesics and/or vasoconstrictors are effective for the acute attack. Initial therapy for mild migraine headache is usually aspirin or other nonsteroidal anti-inflammatory agents (e.g. ibuprofen and naproxen sodium). These analgesics, along with sleep in a quiet, dark room, an ice pack on the head and an antiemetic agent, are often sufficient to treat the mild migraine. The use of antiemetic drugs like metoclopramide (Reglan®) is an important variable in determining how effective analgesic action will be. Migraine attacks seem to cause atony and dilation of the stomach along with closure of the pyloric sphincter thereby impairing absorption of the analgesic medications. This decrease in absorption is probably why individuals with migraines generally complain about the lack of effectiveness of this class of drug. Metoclopramide not only helps with the nausea and the headache, but also improves gastrokinetics, correcting the delayed absorption. More potent vasoconstrictors, like ergotamine tartrate, are often combined with nonsteroidal, anti-inflammatory drugs and anti-emetic therapies for moderate to severe migraine attacks. Ergotamine is a potent vasoconstrictor that has been used since the 1920's as an abortive therapy for migraine episodes. While oral therapy can be employed, rectal suppositories of ergotamine are far more effective because it does not interfere with gastrointestinal function. A 1-mg rectal suppository has been shown to provide complete headache relief within three hours of taking the drug in 73% of patients with migraine.

However, despite ergotamine's effectiveness, it must be used intelligently, as frequent use of the drug results in rebound headache. Abstinence from the vasoconstricting medication for a few hours leads to vasodilation and headache pain. This then perpetuates a vicious cycle in which the patient gets daily headaches, and takes ergotamine on a daily basis. Other ergotamine side effects include nausea, vomiting, abdominal pain, muscle cramps, and occasionally, distal paresthesias. Individuals who take ergotamine on a daily basis may suffer from a condition called ergotism, whose symptoms includes nausea and weakness as well as cold, bluish and tingling extremities.

An intravenous derivative of ergotamine, dihydroergotamine (HE), is an even more potent vasoconstrictor and is typically employed for headaches that persist or are severe in nature, despite initial oral abortive therapy. Both DHE and a new injectable drug called sumatriptan (Imitrex®), work by stimulating the inhibitory presynaptic 5HT receptor at the trigeminovascular junction. A dose of six milligrams of sumatriptan has been shown to reduce the intensity of moderate to severe migraine headaches by 70%. Side effects from this type of drug include distal paresthesias, tingling, heaviness, and a sensation of pressure.

b. Preventive Therapy

In contrast to abortive therapy, preventative drug strategies can be employed if the frequency of migraine attacks is sufficiently high. There are an extremely large number of medications available for migraine prophylaxis. Propanolol, verapamil and methysergide maleate are some of the more commonly employed drugs.

Propranolol is widely prescribed in the United States as a treatment for migraine prevention. Although it has proven to be effective in migraine prophylaxis, its side effects include fatigue, depression, impotence, insomnia, dizziness, and cold extremities.

Another class of antihypertensive medications like propranolol is the calcium channel blockers. Calcium channel blockers were introduced as a class of preventative migraine medications to help antagonize vasoconstriction and prevent cerebral hypoxia. However, research has suggested that they may not be as effective as beta-blockers and, furthermore, that they are associated with numerous adverse events including constipation, fluid retention, drowsiness and hypotension.

Unlike calcium channel blockers or beta-blockers, methysergide is a potent, type 2 serotonin antagonist. For migraine prophylaxis, studies have shown that a 6 mg dose reduces migraine occurrence by more than half in 60% of the patients. However, long-term use of this drug may not be warranted, as it is associated with retroperitoneal fibrosis. As such, a drug hiatus for two to four weeks following six months of continuous use is recommended.

Like pharmacological intervention, non-pharmacological prophylactic therapies may also be highly effective. These include behavioral modification techniques such as stress management, biofeedback, exercise, acupuncture, trigger point injections and numerous physical therapy techniques.

There is currently no formulation, which addresses satisfactorily the needs of a who suffer from migraine headaches. Many of the existing formulations can cause significant side effects. Because of the apparent multi-faceted etiology, some formulations work well for some people but not others.

SUMMARY OF THE INVENTION

The present invention comprises several unique and novel combinations of the following components in a single formulation: an extract of the Feverfew plant, a magnesium salt and riboflavin or, as an alternative embodiment, an extract of the Feverfew plant in combination with a magnesium salt or riboflavin.

DESCRIPTION OF THE DRAWINGS

The invention will be further described with reference to the accompanying drawing in which.

DETAILED DESCRIPTION OF THE INVENTION

Figure 1:
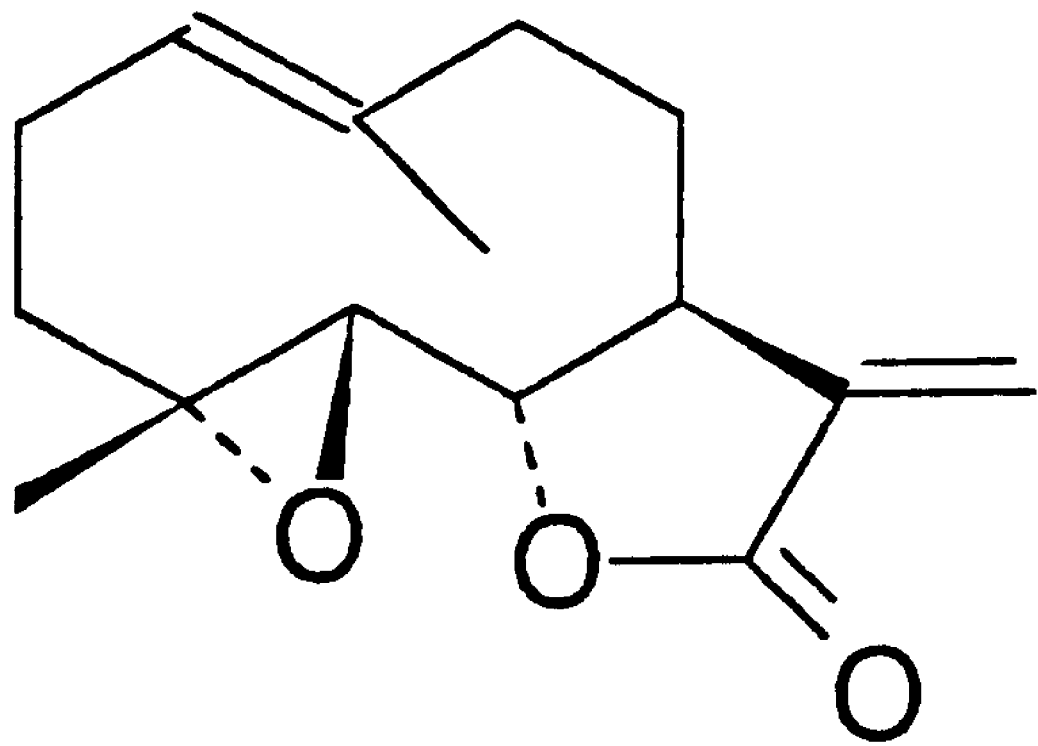
FIG. 1 is a representation of the chemical structure of parthenolide, a major component of the feverfew extracts.

Formulating an effective treatment for any disease, especially one as challenging as migraine headaches, always is difficult. What cause or causes should be addressed and how to best address them are just some of these difficulties. Many compounds have been tested against migraine headaches, some with encouraging results. But which to use, especially in combination with which others, is a most challenging question.

The present invention is based on a particular combination of, compounds, each in a particular dosage range. Tests have shown this combination to be uniquely effective as a dietary supplement in treating migraine headaches.

It should be noted that all of the components of this invention are available commercially from various vendors and that the extracts are standardized to various components normally found within the extract. The Feverfew extract is preferably obtained from Indena, U.S.A., Inc., of Seattle, Wash.

The invention is usually provided in a tablet, but can also be provided in other forms including soft-gel capsule, powder or other methods of packaging. Actual formulation into capsules is handled using industry standard methods of production.

The details of the individual components of the present invention are described below.

Feverfew

Feverfew (*Tanacetum parthenium*) is a member of the daisy family (*Asteraceae*) and is a short, bushy perennial that grows along fields and roadsides. Its yellow-green leaves and yellow flowers resemble those of chamomile, for which it is sometimes confused. The flowers bloom from July to October. The leaves are used in medicinal preparations. Feverfew enjoyed wide use by British herbalists as an analgesic in the treatment of fevers and arthritis, but faded into obscurity. Feverfew has enjoyed a revival over the past two decades due to approval of its use for treatment of migraine by both the Canadian and British governments.

Active Constitute

Feverfew is rich in compounds known as sesquiterpene lactones (STL). The most important of these compounds is parthenolide (see FIG. 1). First identified in 1960, parthenolide represents about 85% of the STL content in feverfew and is the portion of the leaf believed to be responsible for feverfew's anti-migraine activity. Other lactones include chrysanthenyl and michefuscalide.

A critical consideration in commercial feverfew products has been the highly variable content of parthenolide. An analysis of commercial feverfew products in Canada found about half are virtually devoid of this compound. As a minimal standard, the Health Protection Branch of the Health and Welfare Department of the Canadian Government has proposed that feverfew preparations should contain at least 0.2% parthenolide content.

The sesquitepene lactones are typically extracted from feverfew using an alcohol or alcohol/water extractant. However, other extraction means such as steam extraction or other solvent systems, included non-acqueous systems may be used to recover and isolate the active ingredients.

Mechanism of Action

Feverfew, and specifically parthenolide, inhibits platelet aggregation and histamine release. It has also been shown to inhibit release of serotonin from platelets and polymorphonuclear leukocyte granules. This is believed to reduce the severity, duration and frequency of migraine headaches and lead to an improvement in blood vessel tone.

Feverfew also inhibits prostaglandin synthesis and the release of arachidonic acid. This action may explain its historical use for inflammatory conditions such as arthritis Clinical Applications.

Clinical studies with feverfew have focused on the treatment and prevention of migraine and have primarily taken place in Great Britain. These studies indicate the efficacy of feverfew as a useful tool in the long-term management of migraines.

The initial clinical study enrolled migraine patients who had been using feverfew for several years. Seventeen patients were enrolled and given either feverfew (50 mg daily) or placebo. Eight patients, who remained on feverfew, experienced continued relief of migraines over a six month period. The nine receiving placebos had an almost three-fold increase in migraines. Many of these headaches were incapacitating, and anxiety, insomnia and muscle and joint soreness were also reported. This has prompted some concern at the abrupt cessation of feverfew therapy.

A second study enrolled 72 migraine sufferers. They received either 82 mg of feverfew (containing approximately 500 mcg of parthenolide) daily or placebo. Treatment with feverfew for four months led to a decreased incidence and severity of migraines. Feverfew also led to less vomiting attacks and fewer visual disturbances during migraine attacks. Adverse events were mild (primarily mild gastrointestinal nervousness) and did not result in discontinuation of treatment.

Previously Recommended Dosages

Appropriate dosing of feverfew leaf for migraine prophylaxis is based on parthenolide content. The Canadian Health Protection Branch has granted a Drug Identification Number (DIN) for feverfew. They recommend a daily dosage of 125 mg of a dried feverfew leaf preparation from authentic *tanacetum parthenium* containing a minimum of 0.2% parthenolide for migraine prevention. This translates to a daily parthenolide dosage of at least 250 mcg. This should be considered a minimum amount for efficacy. Whether considerably higher doses of parthenolide might offer greater results has yet to be proven. Continuous use for at least four to six weeks is recommended.

Side Effects/Contraindications

In addition to the adverse events listed in the clinical studies above, the most common side effect reported with feverfew has been mouth ulceration. This has predominantly been found in individuals chewing the leaves. Scattered reports of dermatitis have been reported with use of feverfew. To date, no long-term toxicity studies have been performed.

Magnesium

Research had indicated that various factors, which are known to trigger migraines (namely stress, pregnancy, menstruation, alcohol ingestion, and some diuretics) also, promote magnesium wasting. In addition, magnesium exerts many of the same effects as drugs that are helpful in the prevention or treatment of migraines. These effects include: (1) inhibition of vasospasm; (2) inhibition of platelet aggregation; (3) stabilization of cell membranes; (4) interference with the synthesis, release or action of inflammatory mediators; and (5) alterations in cerebral vascular tone. In addition, brain magnesium concentrations (as measured by NMR spectroscopy) were significantly lower by 19% in-patients during a migraine attack than in healthy controls. These observations suggest that magnesium may play a role in the prevention and/or treatment of migraine.

Magnesium has also been given intravenously to treat acute episodes of migraine. Forty patients with an acute migraine attack were given 1.0 g of magnesium sulfate (in a 1.0% solution) over five minutes. Fifteen minutes after the infusion, 35 patients (8.5%) experienced at least a 50% reduction in pain. Nine patients (22.5%) had complete relief of pain. In 21 of the 35 patients who improved, relief persisted for 24 hours or more. The effectiveness of magnesium was related to the pretreatment serum concentration of ionized magnesium. Of the 21 patients whose serum ionized magnesium level was below 0.54 mmol/I, 18 cases (86%) experienced pain relief, which lasted at least 24 hours. In contrast, lasting relief occurred in only 3 (16%) of 19 patients whose serum ionized magnesium concentration was at or above 0.54 mmol/I ($p<0.001$). This study suggests that intravenous administration of magnesium is an effective treatment for acute migraine attacks, particularly in-patients whose serum ionized magnesium concentrations are low.

These studies provide a rationale for oral magnesium supplementation for migraine prophylaxis. A reasonable dosage is 200 to 600 mg/day. Intravenous administration of magnesium may also be considered as a method of aborting acute migraine attacks. While measurement of serum ionized magnesium might be useful to predict which patients are most likely to respond to intravenous magnesium, this test is not yet commercially available.

Riboflavin

Riboflavin is the precursor of flavin adenine dinucleotide (FAD), a coenzyme involved in the electron-transport chain. A deficiency of mitochondrial energy reserve has been observed between attacks in-patients with migraines. Theoretically, this defect might be ameliorated by compounds such as riboflavin which enhance the activity of the electron-transport chain.

To test that theory, 49 patients with recurrent migraines were given riboflavin, 400 mg/day with breakfast, for at least three months. The mean number of migraine attacks fell by 67% and migraine severity improved by 68%. One patient stopped treatment because of gastric intolerance, but no other side effects were reported. This study suggests that riboflavin supplementation may reduce the recurrence rate of migraines.

Although data on the effect of riboflavin remain preliminary, this vitamin is inexpensive and safe.

Combinations of Feverfew & Riboflavin

Lazorowych et al. WO96/22774 teaches the use of feverfew and riboflavin as a treatment for migraine. They then suggest the addition of a small amount of magnesium, at page 12, line 29, where it is indicated that an extremely small quantity of magnesium, in the form of 8 gm of magnesium stearate, be added to 1000 gm of a mixture comprising 60 gm of feverfew and 750 gm of riboflavin. Magnesium stearate contains only 4% magnesium. As a result, the reference teaches adding an extremely small quantity of magnesium, namely 0.16 mg to a composition containing 750 gm of riboflavin and 60 gm of feverfew. Still further, while the reference teaches the use of standardized feverfew leaf rich in susquitepene lactones, such standardized leaf is described as containing only 0.125–0.5% parthenolide and, in the preferred composition 0.2% parthenolide.

Preferred Embodiment

From these and other studies, it appears that a combination of feverfew extract with a therapeutically effective amount of STL, particularly parthenolide, combined with either or both, therapeutically effective amounts of magnesium and riboflavin, is especially effective in treating migraine headache.

In contrast to Lazorowych et al, applicant's compositions all include significant quantities of magnesium present as a combination of magnesium oxide and a salt of an organic acid, preferably magnesium citrate. This combination of magnesium compounds provides a unique and distinctive advantage in that it allows delivery of high quantities of magnesium in a body absorbable form without common side effects encountered in other treatment modalities that incorporate magnesium. Further, applicant's preferred embodiment utilizes an extract of feverfew standardized with at least about 0.7% parthenolide. Still further, Examples 1 and 2 of WO96/22774 teaches capsules or tablets, which do not contain magnesium, consisting of about 120 to 125 mg of feverfew leaf with 400 mg of riboflavin (approximately 30% feverfew leaf). However, when even a small quantity of magnesium is added (WO96/22774, Example 4) the amount of riboflavin is increased to 750 mg and the feverfew leaf is significantly reduced to 60 mg (7.5% in relationship to the riboflavin), with the magnesium constituting only 0.04% of the feverfew/riboflavin/magnesium stearate composition (4% of 8 gm in a combination including 750 gm riboflavin and 60 gm feverfew). Applicant's preferred unit comprises 37.5% magnesium.

More particularly, the magnesium is provided as a mixture of magnesium oxide and a magnesium salt of an organic acid. While magnesium citrate is the magnesium salt of choice, magnesium acetate, formate, methionate, aspartate, lactate, glutamate, oxalate, pyrrollidone carboxylate or other organic acids, for example, may be used. (Durlach, J. "Present and Future of Magnesium Research" *J. of Jap. Soc for Magnesium Research.* 1993 Vol. 12 2:113–135) Magnesium citrate is a compound which has a relatively high concentration of magnesium (16.16%) and is recognized to be non-toxic over a wide dosage range and readily absorbable by the body. Other organic acid magnesium salts with high concentrations of magnesium which may be used include, but are not limited to, magnesium acetate (17% mg) magnesium formate (21.26% mg), magnesium lactate (12% mg), and magnesium oxalate (21.64% mg). However before using these alternatives, the solubility, availability of the magnesium ion and the toxicity should be evaluated. For example, the oxalate may be insoluble.

Also, it is preferred to use a feverfew extract with a higher concentration of parthenolide, preferably about 0.7% parthenolide. However, it is also possible to use larger quantities of a feverfew extract with a lower concentration of parthenolide. For example, in place of 50 mg of feverfew having a 0.7% parthenolide, 175 mg of feverfew extract with 0.2% parthenolide could be used.

Feverfew extracts with higher parthenolide concentrations can also be used and these extracts may be encapsulated to modify their rate of release to the body. For example, Biodar, Ltd. of Yevna, Ireal offers a microencapsulated feverfew extract containing 2.0% parthenolide (Fever Cote® 2) as well as a slow release microencapsulated feverfew extract containing 0.5% parthenolide which is released in the body at a fairly constant rate over 12 hours. (Fever Cote® 0.5 SR). Slow release extracts with up to 2% parthenolide are available.

The preferred embodiment is a unit dosage form, which could be a tablet, a measured amount of powder, a capsule or other like form, containing a composition comprised of the following components:

1. 50 milligrams of feverfew extract standardized to 0.7% parthenolide, and
2. 150 milligrams of Magnesium preferably as a 1:1 ratio of magnesium citrate and magnesium oxide, and
3. 200 milligrams of riboflavin.

This preferred composition contains 0.35 mg pathenolide with 150 mg of magnesium for a ratio of magnesium, to parthenolide of about 430:1. With this embodiment, the unit dose should be taken as a dietary supplement, two times each day to provide the desired level of treatment. The daily dosage would then contain sufficient feverfew extract to provide about 0.7 mg of parthenolide, about 300 mg of magnesium as a combination of magnesium oxide and a magnesium salt of an organic acid and about 400 milligrams of riboflavin.

While the preferred embodiment comprises a capsule with 50 mg of 0.7% parthenolide, 150 gm magnesium and 200 mg riboflavin delivered twice a day, it is contemplated that certain patients may require larger dosages (2 or 3 times) or more dosages (up to 4) over a 24 hour period.

It is also contemplated that microencapsulation and other drug release controlling technology would allow production of a single pill containing larger quantities of the components for release over an extended period of time. Altenatively, improved treatment may result from extended release of the same or greater total quantities of the components rather than a high initial deliver of the components which occurs soon offer ingestion of a unit dose, which is typical of pills or capsules containing water soluble absorbable constituents. It is also contemplated that it may be desirable to rapidly deliver one or two of the components of the preferred composition fairly rapidly while delivering the remaining constituents over an extended period of time. Alternatively, concentrations of the active ingredients may be increased or decreased up to 50% in comparison to the other constituents to address certain migraine variants or related headache symptoms.

Another alternative is to provide additives which enhance the absorption and utilization by the body of the active ingredients. For example, it is known that vitamin B12 can enhance the absorption of riboflavin by the body.

It is contemplated that other additives may be added to supplement the effect of the active ingredients or provide addition therapeutic effects. Also, it is contemplated that other constituents normally present along with the above described active ingredients may have a beneficial effect. For example, in preparing a feverfew extract containing effective amounts of parthenolides, other compounds present in feverfew are also extracted. For example, the extract may also include essential oils including but not limited to chrysanthenyl acetate. A beneficial effect may result from including 0.2 to 0.4%$_w$ of essential oils, of which 0.01 to 0.3%$_w$ is chrysanthenyl acetate. Alternatively, chrysanthenyl acetate, or essential oils including chrysanthenyl acetate may be extracted from other plants and added to the preferred composition. For example, chrysanthenyl acetate can be extracted from Centipeda cunninghemi and related plants (U.S. Pat. No. 5,804,206).

It is clear from studies, that the amount of each of the components administered on a per unit time basis is the important factor. How the components are distributed between dosage form and the actual number is not important.

Likewise, the actual percentage of STL, as measured by parthenolide, within the Feverfew extract could vary over a reasonable range as long as the actual amount of the Feverfew extract is adjusted in order to provide the same therapeutically effective dose.

Studies with the preferred embodiment have shown a significantly greater percentage of symptomatic relief than would be expected from the individual components alone. In addition to the improved cerebrovascular tone, patients receiving the preferred embodiment have significantly reduced occurrence of migraine headaches, decreased sensitivity to light and sound, reduced nausea and increased mobility.

As an alternative to the preferred embodiment, combinations of Feverfew extract and either riboflavin or magnesium are also believed to be effective in reducing the symptoms of migraine headaches.

No previously known dietary supplement has provided in a single treatment the wide range of therapeutic benefits that are provided by the instant invention. All components have been included in the present invention at known therapeutically effective amounts in order to provide broad-spectrum therapeutic benefits with minimal side effects. Though the preferred embodiment includes feverfew extract, riboflavin and magnesium, combinations of feverfew extract plus riboflavin and feverfew extract plus magnesium should also prove effective.

In addition, having all components available in a single formulation provides cost savings for the patient and more efficient treatment protocols for the physician.

EXAMPLE 1

This patient is a 30-year-old woman who has had a seven-year history of migraines. Typically she would wake in the morning with a migraine headache which would only get worse as the day wore on. The headaches in the morning would include sharp razor like pains in the right eye and intense throbbing headache on the right side of her head. Often a mild migraine would always progress into a full on migraine, which included extreme sensitivity to light and sound and nausea, which would result in vomiting 10–20 times a day.

After using the preferred embodiment as a dietary supplement, the occurrence rate was significantly reduced with mild occurrences often dissipating without escalating to a full migraine and often without the use of prescription medicines. In addition, the nausea was absent. The patient's mobility was enhanced significantly.

While suffering a full migraine, the patient would be bed-ridden because of hypersensitivity to light, sound and movement. While under treatment with the preferred embodiment, the patient was no longer bed ridden by the migraine attacks and was able to sit, stand, work and walk slowly.

The reduction of the nausea has permitted the patient, when needed, to take Imitrex®, a prescription medicine. Previously, the nausea was so severe that the patient couldn't keep the medicine down long enough to provide any therapeutic effect.

EXAMPLE 2

A 40-year-old female patient has suffered migraine headaches since puberty. The frequency has ranged from 2 to 10 a month and lasting from a few hours to as long as 40 days.

Patient has sought medical advice from various doctors, therapists and even a neurologist who specialized in headaches. Patient has tried a wide range of therapeutic techniques and devices including biofeedback, meditation and relaxation techniques, physical therapy, chiropractic treatments, acupuncture acupressure, exercise, and dietary modifications.

The patient has taken beta-blockers, inhalers, Midrin, Imitrex® injections, Fiorinal and Demerol injections, all of, which had varying success with varying side effects.

After using daily dosages of the preferred composition, the patient was migraine free for the first two months. On longer use, the patient rarely had migraine headaches, and when she did, the pain is much less severe and the duration is much less.

EXAMPLE 3

Under the care of a physician, over 100 patients diagnosed with migraine headaches were treated with a daily dosage of 400 mg of riboflavin, 100 mg of a feverfew extract (0.7% parthenolid) and 300 mg of magnesium, with 150 mg of the magnesium provided by magnesium oxide and 150 mg of the magnesium provided by magnesium citrate. The majority of these patients had suffered from migraine headaches, which had failed to adequately respond to any of the current treatments or combination of treatments presently available. The composition was found to be highly effective in the treatment of frequent migraine headaches, even where no other treatments were successful. All of these patients showed a reduction in the frequency, duration and severity of migraine attacks. In the opinion of the treating physician, the clinical benefits obtained using this composition were far greater than expected from a mere combination of the individual components.

Although the invention has been described with reference to particular disclosures, it is to be understood that the invention is not limited to these particular disclosures and extends to all equivalents within the scope of the claims.

I claim:

1. A dietary supplement comprising an extract from the feverfew plant, magnesium and riboflavin, said extract containing parthenolide and the magnesium is provided as a combination of magnesium oxide, and a magnesium salt of an organic acid and the ratio of magnesium to parthenolide is at least about 430:1.

2. A dietary supplement comprising an extract from the feverfew plant and magnesium, said extract containing parthenolide, said magnesium being provided as a combination of magnesium oxide and a magnesium salt of an organic acid and the ratio of magnesium to parthenolide is about 430:1.

3. A method for reducing the symptoms of migraine headaches comprising the steps of administering a therapeutically effective amount of a dietary supplement comprising an extract of the Feverfew plant, riboflavin and magnesium wherein said extract contains parthenolide and the magnesium is provided as a combination of magnesium oxide and a magnesium salt of an organic acid.

4. A method of reducing the symptoms of migraine headaches comprising the steps of administering a therapeutically effective amount of a dietary supplement comprising an extract of feverfew plant, and magnesium wherein the magnesium is provided as a combination magnesium oxide and a magnesium salt of an organic acid.

5. The dietary supplement of claim 1 wherein the feverfew extract contains about 0.7% panthenolide.

6. The dietary supplement of claim 2 wherein the feverfew extract contains about 0.7% panthenolide.

7. The method of claim 3 wherein the feverfew extract contains about 0.7% pathenolide.

8. The dietary supplement of claim 1 wherein a unit dose has the parthenolide present in an amount of about 0.35 milligrams per dose, the riboflavin present in an amount of about 200 milligrams per dose and the magnesium present in an amount of about 150 milligrams per dose.

9. The dietary supplement of claim 8 wherein a daily dosage is at least two unit doses.

10. A method of reducing the symptoms of migraine headaches comprising the steps of administering a daily dosage of a dietary supplement comprising: 0.70 milligrams of parthenolide and 300 milligrams of magnesium, wherein the magnesium is provided as a combination of magnesium oxide and a magnesium salt of an organic acid, the magnesium salt selected from the group consisting of magnesium citrate, magnesium acetate, magnesium formate, magnesium lactate, and magnesium oxalate.

11. The method of claim 10 further comprising the delivery, on a daily basis, of 400 milligrams of riboflavin.

12. A dietary supplement comprising 0.70 milligrams of parthenolide and 300 milligrams of magnesium, wherein the magnesium is provided as a combination of magnesium oxide and a magnesium salt of an organic acid, the magnesium salt selected from the group consisting of magnesium citrate, magnesium acetate, magnesium formate, magnesium methionate, magnesium aspartate, magnesium lactate, magnesium glutamate, magnesium pyrollidone carboxylate, and magnesium oxalate.

13. The dietary supplement of claim 1 wherein one or more of the extract, magnesium and riboflavin are present in a form releasable after ingestion over a period of up to about 12 hour.

14. The dietary supplement of claim 1 further including essential oils constituting from about $0.2\%_w$ to about $0.4\%_w$ of the extract.

15. The dietary supplement of claim 14 wherein the extract contains from about $0.1\%_w$ to about $0.3\%_w$ of chrysanthenyl acetate and at least about 0.7%, parthenolide.

16. A method of reducing the symptoms of migraine headache comprising administering a therapeutically effective amount of parthenolide, a magnesium salt and riboflavin, the magnesium salt being provided as a salt of an organic acid.

17. The dietary supplement of claim 16 comprising 0.70 milligrams of parthenolide and 300 milligrams of magnesium wherein the magnesium is provided as a combination of magnesium oxide and a magnesium salt of an organic acid, the magnesium salt selected from the group consisting of magnesium citrate, magnesium acetate, magnesium formate, magnesium methionate, magnesium aspartate, magnesium lactate, magnesium glutamate, magnesium pyrollidone carboxylate, and magnesium oxalate.

18. The method of claim 16 wherein the parthenolide is provided by feverfew.

19. The method of claim 16 wherein the parthenolide is provided as an extract of feverfew.

20. The method of claim 16 further including magnesium oxide.

21. The method of claim 16 wherein a unit dose contains parthenolide, riboflavin and magnesium in ratios of about 200 milligrams of riboflavin, about 150 milligrams of magnesium and up to about 0.35 mg parthenolide.

22. A method of reducing the symptoms of migraine headache comprising administering a therapeutically effective amount of a composition wherein the active ingredients consist essentially of about 42.8% by weight of magnesium and about 57.1% by weight of riboflavin, the balance of the active ingredients being parthenolide.

23. The method of claim 22 wherein the parthenolide is present in a concentration of about 0.1% by weight.

* * * * *